US00PP09620P

United States Patent [19]

Guillou et al.

[11] Patent Number: Plant 9,620

[45] Date of Patent: Aug. 6, 1996

[54] GERANIUM PLANT NAMED 'GUIVIN'

[75] Inventors: Jacques Guillou; Bernard Guillou; Maurice Guillou, all of Saint-Malo, France

[73] Assignee: Ets, Guillon Freres, Saint-Malo, France

[21] Appl. No.: 384,523

[22] Filed: Feb. 1, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,381 9/1993 Klemm ..... Plt./87.12

*Primary Examiner*—James R. Feyrer

*Attorney, Agent, or Firm*—Foley & Lardner

[57] ABSTRACT

A new and distinct cultivar of geranium plant named Guivin, characterized by its purple and double-type flowers, medium-green foliage, zonation that is absent or very weak which forms a ring near the base of the leaf, compact and good branching plant habit.

1 Drawing Sheet

The present invention comprises a new and distinct cultivar of geranium, botanically known as *Pelargonium peltatum l'Hert,* and hereinafter referred to by the cultivar name Guivin.

Guivin is a product of a planned breeding program which had the objective of creating new geranium cultivars with blue-red flower color and compact and well branched growth habit.

Guivin was originated from a hybridization made in a controlled breeding program in Saint Malo, Bretagne, France in 1985.

The female and male parents were unnamed hybrids from the proprietary Guillou collection, both parents being characterized by blue-red, semi-double flowers.

Guivin was discovered and selected as one flowering plant within the progeny of the stated cross by the inventors in 1986 i a controlled environment in Saint Malo, Bretagne, France.

The first act of asexual reproduction of Guivin was accomplished when vegetative cuttings were taken from the initial selection in July 1990 in a controlled environment in Saint Malo, France by a techanician working under the supervision of the inventors. Horticultural examination of selected units initiated in 1990 in Halderen, The Netherlands, has demonstrated that the combination of characteristics as herein disclosed for Guivin are firmly fixed and are retained through successive generations of asexual reproduction.

Guivin has not been observed under all possible environmental conditions. The phenotype may vary with variations in environment such as temperature, light intensity, and daylength without a change in the genotype of the cultivar. The following observations, measurements, and comparisons describe plants grown in Haalderen, Holland under greenhouse conditions which approximate those generally used in commercial practice.

The following traits have been repeatedly observed and are determined to be basic characteristics of Guivin which, in combination, distinguish this geranium as a new and distinct cultivar:

1. Purple and double-type flowers.
2. Medium-green foliage.
3. Absent to very weak zonation which forms a ring near the base of the leaf.
4. Compact plant habit.
5. Good branching habit.

Of many commercial cultivars known to the present inventors, there is no cultivar with which Guivin can be closely compared.

The accompanying color photographic drawings show typical flower and foliage characteristics of Guivin.

Figure 2:
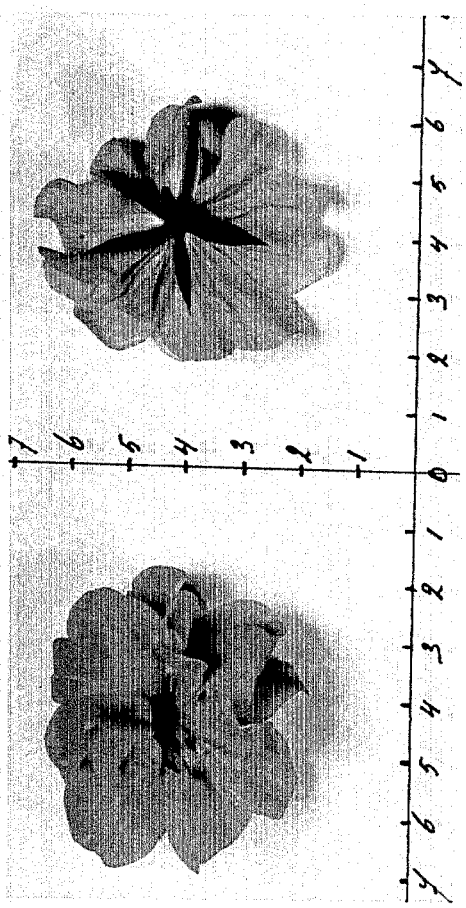
FIG. 2 is a top and bottom view of an individual flower from Guivin.
Figure 3:
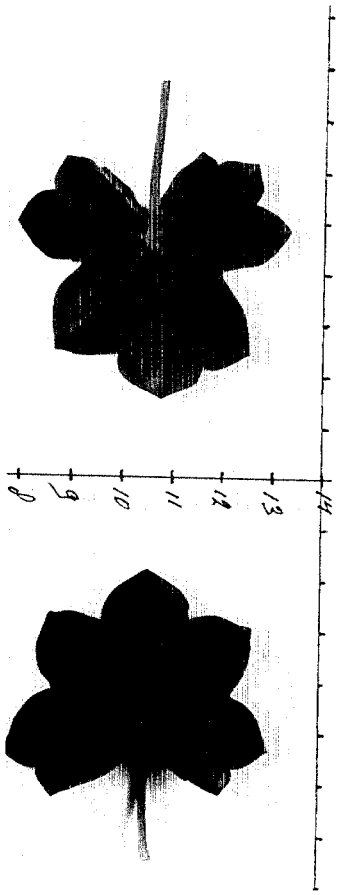
FIG. 3 is a top and bottom view of an individual leaf from the cultivar.
Figure 1:
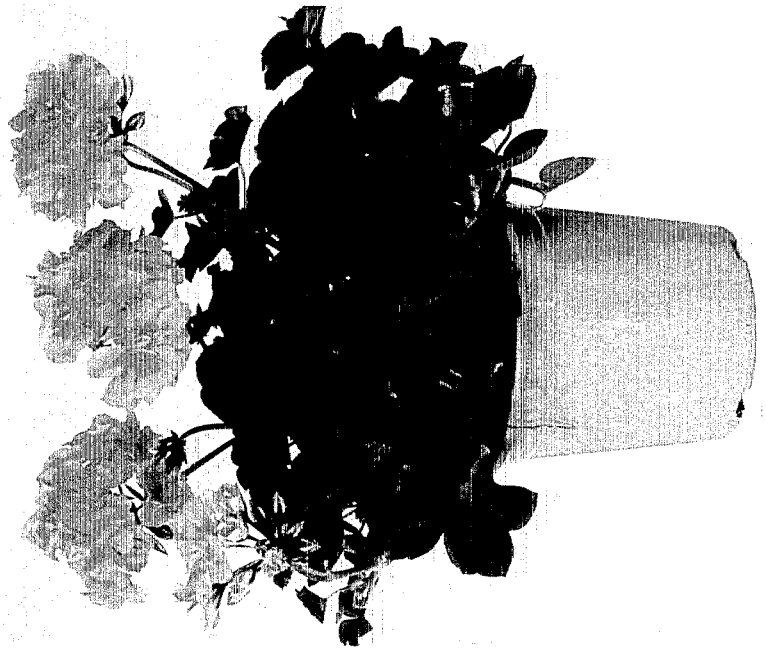
FIG. 1 is a side view of the cultivar.

In the following description, color references are made to The Royal Horticultural Society (R.H.S.) Colour Chart. The color values were determined indoors in 1991 under greenhouse conditions in Hannover, Germany with colors being as true as possible with illustrations of this type.

Classification:

*Botanical.—Pelargonium peltatum l'Hart* cv. Guivin.

Commercial.—Ivy geranium, Guivin.

INFLORESCENCE

A. Umbel: Nearly semi-spherical with 6 to 8 buds per umbel.
- *Average diameter.*—92 mm.
- *Average depth.*—30 mm.
- *Peduncle length.*—95 mm.
- *Pedicel length.*—21 mm.

B. Corolla
- *Average diameter.*—45 mm.
- *Form.*—Double-type with 15 to 20 petals per flower. There are more petals in the spring than fall.
- *Color (general tonality from a distance of three meters).*—Purple.
- *Color (abaxial).*—Blue red (R.H.S. 67B).
- *Color (adaxial).*—Light purple-red (R.H.S. 61D).

C. Bud:
- *Petal size.*—Approximately 20 mm wide and 30 mm long.
- *Petaloid size.*—Approximately 15 mm wide and 25 mm long.
- *Sepal number.*—5.
- *Shape.*—Narrow elliptic.
- *Color (abaxial).*—Green, no anthocyanin.
- *Color (adaxial).*—Purple-red.

D. Reproductive organs:
- *Androecium.*3–7 fertile anthers, white filaments, orange pollen.
- *Gynoecium.*—5–6 lobed stigma, red style and stigma.

E. Spring flowering response period: 1.6 flowers per umbel opened 15 weeks after planting of unrooted cuttings (pinched plants).

F. Outdoor flower production: 80–90 umbels per plant from late April–May through September. Pinching of spent blooms is necessary to ensure continued flowering.

G. Durability: Shatter resistance is good.

PLANT

A. Foliage:

*Form.*—Ivy-shaped.

*Base.*—Partly overlapping.

*Margin.*—Entire with medium undulation.

*Color (abaxial).*—Green.

*Color (adaxial*0.—Meium-green (R.H.S. 139A).

*Color (zonation).*—Brown, absent to very weak.

*Variegation.—Absent.*

B. General appearance and form:

*Internode length.*—30 to 40 mm.

*Branching pattern.*—5–6 branches per plant that grow horizontally and densely.

*Height.*50 to 55 cm. in August.

*Plant vigor.*—The plant is grows vigorously producing many leaves and flowers.

C. Tolerance to Botrytis: Good.

What is claimed is:

1. A new and distinct cultivar of geranium plant named Guivin, as illustrated and described.

* * * * *